United States Patent [19]

Fiala

[11] Patent Number: Plant 6,957

[45] Date of Patent: Aug. 1, 1989

[54] CRABAPPLE TREE NAMED SERENADE

[75] Inventor: John L. Fiala, Medina, Ohio

[73] Assignee: Chas. Klehm & Son, South Barrington, Ill.

[21] Appl. No.: 213,916

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An ornamental flowering crabapple tree named Serenade, having a graceful semi-weeping and somewhat spreading habit to 12 feet. The large deep rose striped buds open to very delicate soft pink to white blossoms. The flowers have prominent light yellow antlers. The fruit is a burnt orange over gold, and the mint green foliage is somewhat lanceolate.

4 Drawing Sheets

The present invention comprises a new and distinct cultivar of crabapple tree, botanically known as Malus, and hereinafter referred to by the cultivar name Serenade.

The new cultivar was discovered by the inventor in 1958, resulting from a controlled cross made by the inventor of seed parent (*Malus toringoides*×*Malus zumi*) with pollen parent (*Malus zumi,* 'Golden Candles'-×*Malus zumi* #768) in Medina, Ohio. Asexual reproduction in the form of softwood cuttings and summer chip budding by applicant in Medina, Ohio, has demonstrated that the combination of charateristics as herein disclosed for the new cultivar are firmly fixed and are retained through successive generations of asexual reproduction.

Serenade has not been observed under all possible environmental conditions. The phenotype may vary significantly with variations in environment such as temperature, light intensity, day length, available soil moisture, soil nutrients and pH level.

The following observations, measurements, and comparisons describe trees grown at Klehm Nursery, Barrington, Ill., under conditions which approximate those generally used in commercial practice.

The following traits have been repeatedly observed and are determined to be basic characteristics of Serenade, which, in combination, distinguish this crabapple tree as a new and distinct cultivar:

1. Serenade has a graceful, semi-weeping and somewhat spreading habit to 12 feet.
2. The large deep rose striped buds open to very delicate soft pink to white blossoms. The flowers have prominent, light yellow antlers.
3. The fruit is an attractively colorful burnt orange over gold.
4. The new foliage is shiny, mint green, somewhat lanceolate, clean and disease-free all season long.

Of the many commercial crabapple trees known to the inventor, the most similar in comparison to Serenade are the *Malus floribuna* species. Serenade, however, has larger flowers than floribunda, with wider and bigger petals. In addition, Serenade's foliage is slightly darker green with more red on the new stems and flower peduncles.

The accompanying color photographic drawings show typical characteristics of Serenade, with colors being as true as possible with illustrations of this type.

Sheet 1 is a photograph of Serenade in perspective view.

Sheet 2 is a branch of Serenade showing blossoms in varying stages of openness and leaf color.

Sheet 3 shows fully open blossoms of Serenade, the antlers being clearly shown.

Sheet 4 shows mature fruit of Serenade.

In the following description, color references are made to The Royal Horticultural Society Colour Chart (R.H.S.) and are based on color values taken in Barrington, Ill.

TREE

Origin: Seedling.

Parentage:

*Seed parent.*—(*Malus toringoides*×*Malus zumi*).

*Pollen parent.*—(*Malus zumi* 'Golden Candles'-×*Malus zumi* #768).

Classification:

*Botanic.*—*Malus*×cv 'Serenade'.

*Commercial.*—Ornamental flowering crabapple.

Propagation: Chip budding, bench grafting or softwood cuttings.

Branches: Fine textured and graceful (semi-weeping).

Height: 12 to 14 feet at 15 years of age.

Growth habit: Graceful, semi-weeping and somewhat spreading.

Fruit bearing habit: Annual and abundant.

Foliage:

*Size of leaf.*—2" long by 1" wide.

*Shape of leaf.*—Lanceolate, mint green.

*Texture.*—Graceful.

*Color.*—135B.

*Petiole.*—Slightly red on new foliage.

FLOWERS

Buds:

*Color.*—Deep rose pink approximately 60C-D, and striped.

*Size.*—Large.

Date of first bloom: Normally May 10–15.

Date of full bloom: Normally May 15–20.

Color: Mature blossoms are pure white with hint of light pink 36D; prominent light yellow antlers. During opening, colors constantly change from substantial rose tinging to almost pure white.

FRUIT

Date of maturity: Approximately October 15.

Shape: Round.

Skin: Shiny, attractive, contrasts nicely with clean green foliage.

Color: Orange-gold approximately 23B to bright orange, 28A-B.

Insect and disease resistance: Rated very high in resistance to common crabapple diseases; apple scab, cedar-apple rust, fire blight, frog-eye leaf spot, and powdery mildew.

I claim:

1. A new and unique flowering crabapple tree named Serenade, as illustrated and described.

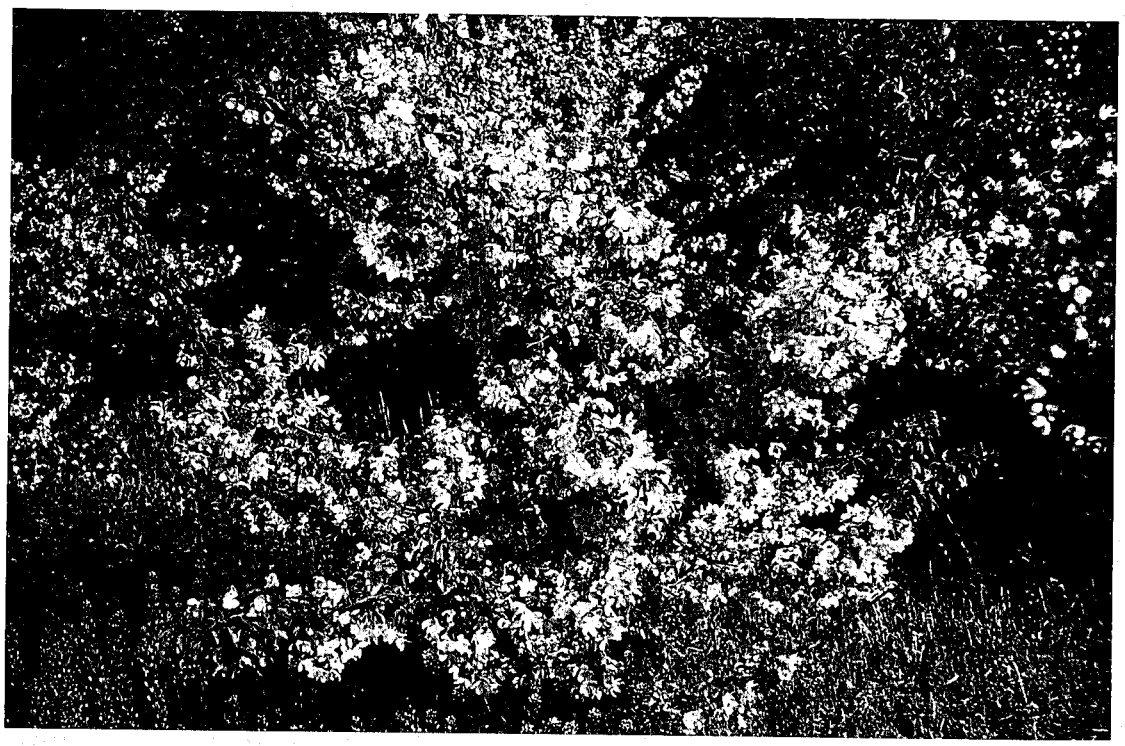

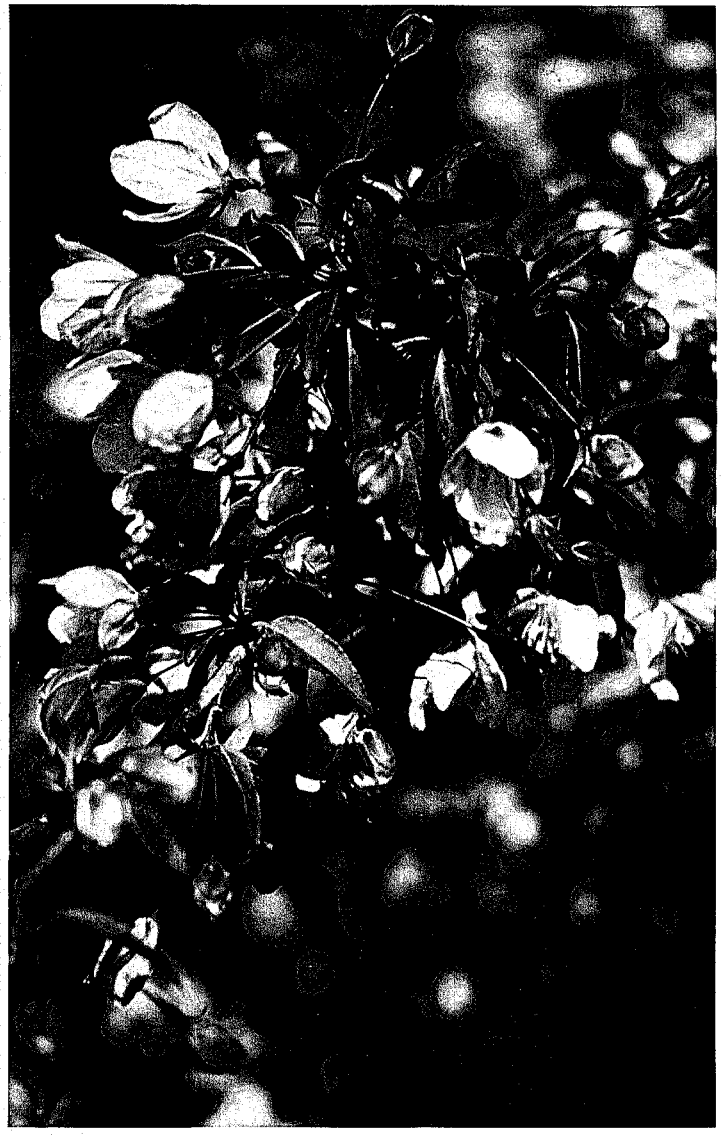

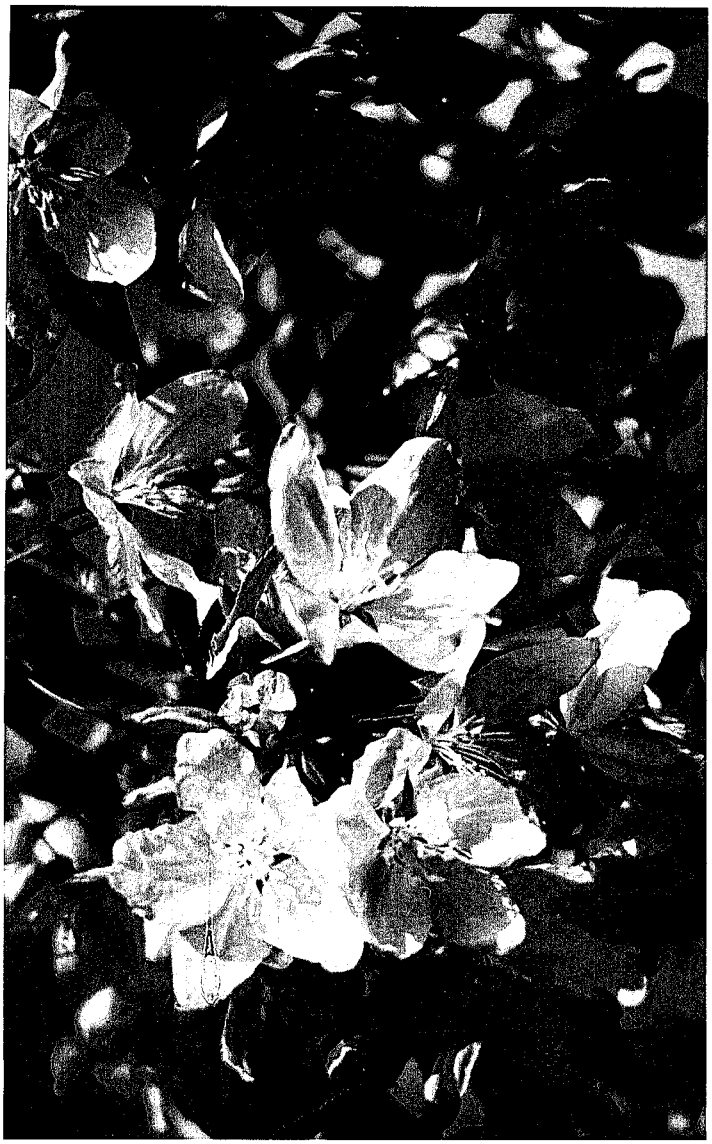

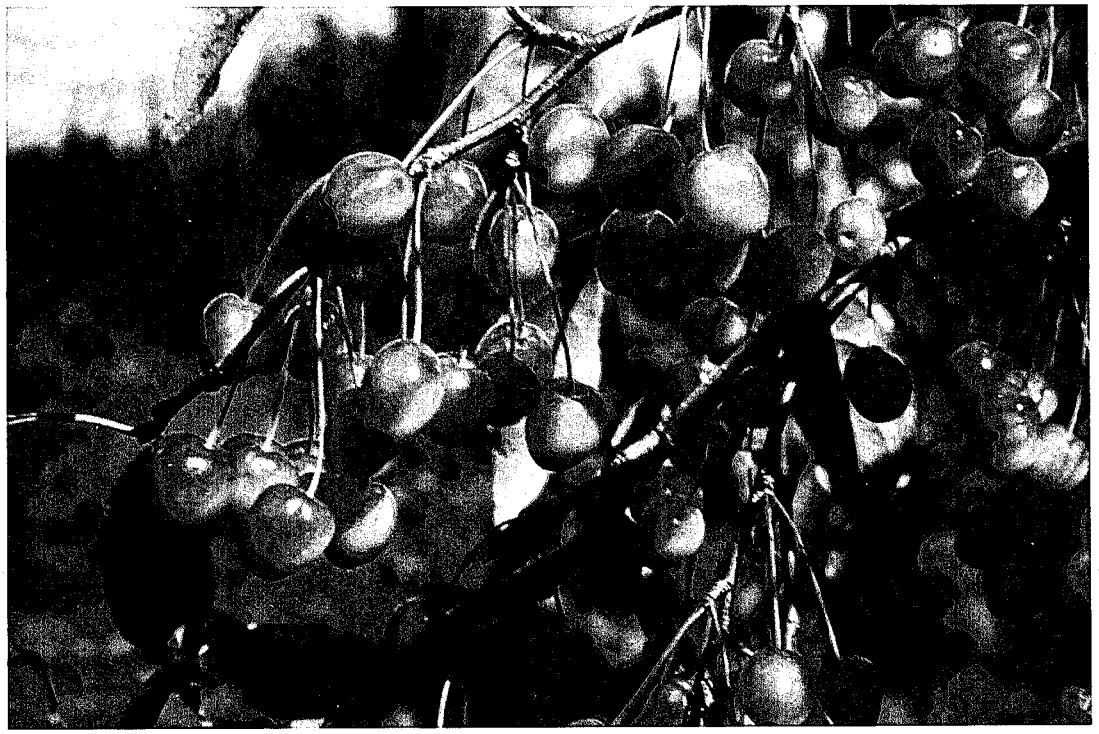

* * * * *